(12) United States Patent
Lewis et al.

(10) Patent No.: US 6,717,004 B2
(45) Date of Patent: *Apr. 6, 2004

(54) METHOD FOR MAKING ALKYLHALOSILANES

(75) Inventors: Larry Neil Lewis, Scotia, NY (US); Alan Carson Crawford, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/207,342

(22) Filed: Jul. 30, 2002

(65) Prior Publication Data

US 2004/0024235 A1 Feb. 5, 2004

(51) Int. Cl.$^7$ .................................. C07A 7/04
(52) U.S. Cl. ....................................... 556/472
(58) Field of Search ........................ 556/472

(56) References Cited

U.S. PATENT DOCUMENTS

| | | | |
|---|---|---|---|
| 2,380,995 A | | 8/1945 | Rochow |
| 5,712,405 A | * | 1/1998 | Nakayama et al. .......... 556/472 |
| 5,783,721 A | * | 7/1998 | Tsumura et al. ............. 556/472 |
| 6,211,394 B1 | | 4/2001 | Kalchauer et al. |
| 6,218,562 B1 | * | 4/2001 | Aramata et al. ............. 556/472 |
| 6,239,304 B1 | * | 5/2001 | Aramata et al. ............. 556/472 |
| 6,258,970 B1 | * | 7/2001 | Ward et al. .................. 556/472 |
| 6,365,766 B1 | | 4/2002 | Aramata et al. |
| 2002/0156310 A1 | | 10/2002 | Inokai et al. |

OTHER PUBLICATIONS

"Catalzyed Direct Reactions of Silicon"—Commercial Production of Silanes by the Direct Synthesis—B. Kanner, K.M. Lewis—1993—pp. 1–66.

"Silicon in Organic, Organometallic, and Polymer Chemistry"—Michael A. Brook—pps. 382–384—1955.

* cited by examiner

Primary Examiner—Samuel Barts
(74) Attorney, Agent, or Firm—Andrew J. Caruso; Patrick K. Patnode

(57) ABSTRACT

A method for making alkylhalosilanes is provided comprising reacting an alkyl halide and silicon in the presence of a copper catalyst comprising copper powder, particulated copper, copper flake, or combinations thereof and at least one co-catalyst.

14 Claims, 4 Drawing Sheets

METHOD FOR MAKING ALKYLHALOSILANES

BACKGROUND OF THE INVENTION

The present invention relates to a method for making alkylhalosilanes. More particularly, the present invention relates to a method for making alkylhalosilanes which includes silicon, alkyl halide and copper catalyst.

Rochow, U.S. Pat. No. 2,380,995 discloses preparing a mixture of alkylhalosilanes by a direct reaction between powdered silicon and an alkyl halide in the presence of a copper-silicon alloy. This reaction is commonly referred to as the "direct method" or "direct process." The reaction can be summarized as follows:

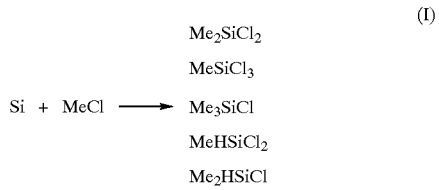

where Me is methyl.

In addition to the above methylchlorosilanes, "residue" is also formed during the production of methylchlorosilane crude. Residue means products in the methylchlorosilane crude having a boiling point greater than about 70° C., at atmospheric pressure. Residue consists of materials such as disilanes for example, symmetrical 1,1,2,2-tetrachlorodimethyldisilane; 1,1,2-trichlorotrimethydisilane; disiloxanes; disilymethylenes; and other higher boiling species for example, trisilanes; trisiloxanes; trisilmethylenes; etc.

Generally, it is desirable to yield high rates of production in the methylchlorosilane reaction as well as selectively produce dimethyldichlorosilane over the other products. New techniques are constantly being sought to improve the alkylhalosilane reaction.

SUMMARY OF THE INVENTION

The present invention provides a method for making alkylhalosilanes comprising reacting an alkyl halide and silicon in the presence of a copper catalyst comprising copper powder, particulated copper, copper flake, or combinations thereof and at least one co-catalyst.

DETAILED DESCRIPTION OF THE INVENTION

Figure 1:
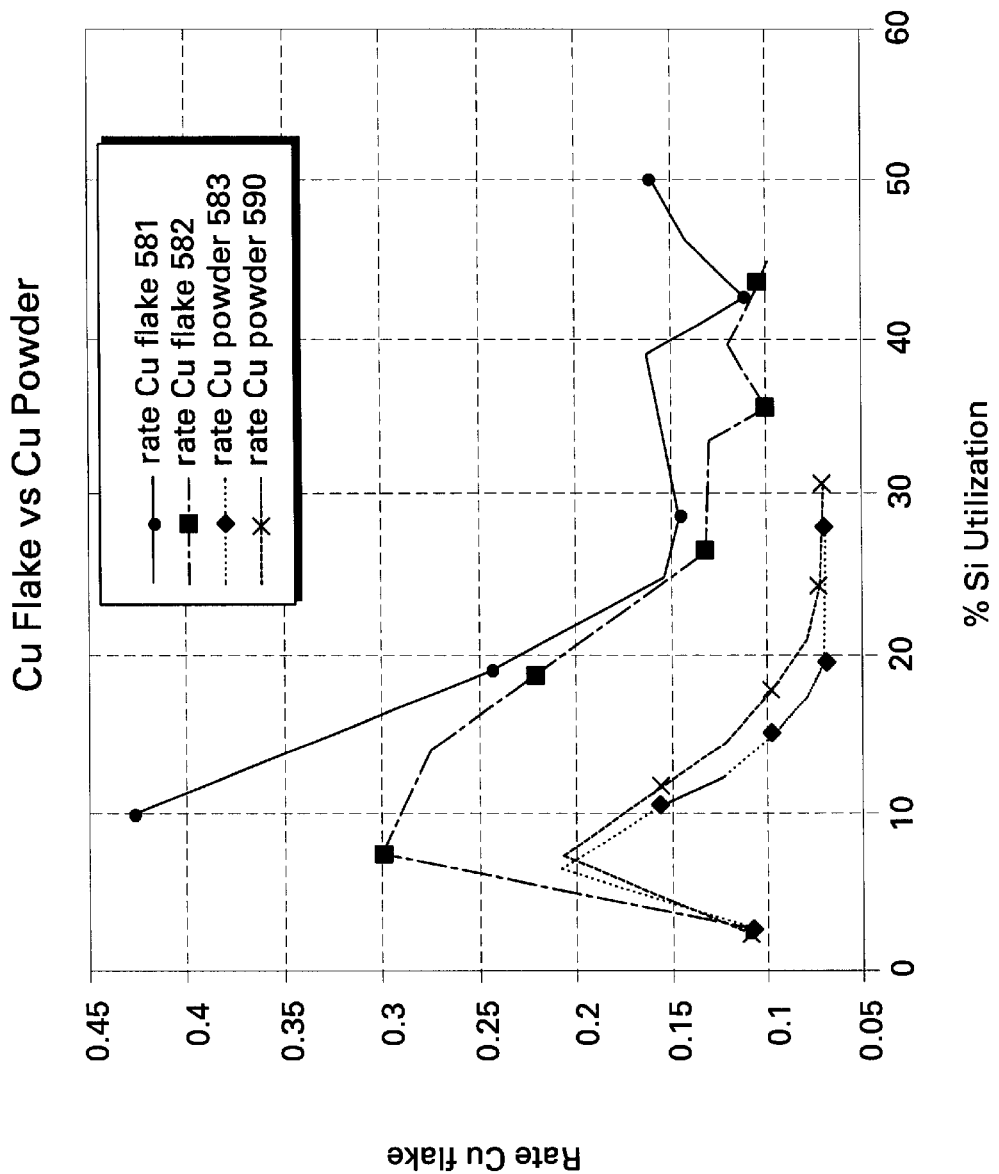
FIG. 1 shows the rate of crude methylchlorosilane formation from duplicate runs of the methylchlorosilane reaction using either copper flake catalyst or copper powder catalyst.

In the present invention, alkylhalosilanes are prepared by reacting silicon and an alkyl halide in the presence of a copper catalyst and at least one co-catalyst. The copper catalyst is in the form of copper powder, particulated copper, copper flake, or combinations thereof. Copper powder, particulated copper, copper flake, or combinations thereof have been found to be suitable and cost effective catalyst for the formation of alkylhalosilanes. Typically, the copper powder, particulated copper, copper flake, or combinations thereof has a surface area greater than 0.2 square meters per gram ($m^2/g$). The copper powder, particulated copper, copper flake, or combinations thereof is typically present in a range between about 1% and about 6% by weight relative to the entire reactor bed, preferably in a range between about 1.5% by weight and about 4.5% by weight relative to the entire reactor bed, and more preferably in a range between about 2% and about 4% by weight relative to the entire reactor bed. Optimum amounts of a given reactant can vary based on reaction conditions and the identity of other constituents can be readily determined by one skilled in the art.

Silicon used in the contact mass can have an iron (Fe) content in a range between about 0.1% and 1% by weight based on total silicon, calcium (Ca) content in a range between about 0.01% and 0.2% by weight based on total silicon, and an aluminum (Al) content in a range between about 0.02% and 0.5% by weight based on total silicon. The silicon typically has a particle size below about 700 microns, with an average size greater than about 20 microns and less than about 300 microns. The mean diameter of the silicon particles is preferably in the range between about 100 microns and about 150 microns. Silicon is usually obtained at a purity of at least about 98% by weight of silicon and it is then comminuted to particles of silicon in the above-described range for preparation of a contact mass. "Contact mass" as used herein refers to a source of copper which is pre-heated with a silicon powder to form a contact mass. The contact mass may be prepared by heating silicon and the copper catalyst in the presence of methyl chloride or other suitable gases at a temperature in a range between about 280° C. and about 400° C. in a furnace.

During the alkylhalosilane reaction, co-catalysts such as zinc, tin, antimony, and phosphorus may be used. Zinc metal, halides of zinc, for example zinc chloride and zinc oxide have been found effective as components for the co-catalyst of the present invention. Zinc (Zn) may be present in a range between about 0.01 weight % and about 1 weight % relative to the entire reactor bed.

Tin metal dust (−325 ASTM mesh), tin halides, such as tin tetrachloride, tin oxide, tetramethyl tin, and alkyl tin halide, and combinations thereof also can be used as a source of tin for making the co-catalyst component of the mass. Tin (Sn) may be present in a range between about 10 parts per million and about 100 parts per million relative to the entire reactor bed.

When phosphorus is a component of the alkylhalosilane reaction, it is typically present in a range between about 100 parts per million and about 1000 parts per million relative to the entire reactor bed. When phosphorus is added to the reactor bed, it can be supplied from a variety of sources. For instance, the phosphorus source can be copper phosphide, zinc phosphide, phosphorus trichloride, alkylphosphines such as triethylphosphine or trimethylphosphine or combinations thereof.

Although methyl chloride is preferably used in the alkylhalosilane of the present invention, other $C_{(1-4)}$ alkylchlrides, for example ethyl chloride, propyl chloride, etc., can be used. Correspondingly, the term "alkylhalosilane" includes dimethyldichlorosilane referred to as "D" or "Di", which is the preferred methylchlorosilane referred to as "T" or "Tri", and a variety of other silanes such as tetramethylsilane, trimethylchlorosilane, methyltrichlorosilane, silicon tetrachloride, trichlorosilane, methyldichlorosilane and dimethylchlorosilane. Dimethyldichlorosilane has the highest commercial interest. A T/D ratio is the weight ratio of methyltrichlorosilane to dimethyldichlorosilane in the crude methylchlorosilane reaction product. An increase in the T/D ratio indicates that there is a decrease in the production of the preferred dimethyldichlorosilane. Hence, the T/D product ratio is the object of numerous improvements to the alkylhalosilane reaction.

In addition to T/D ratio, another measure of performance of the methylchlorosilane reaction is the rate of crude methylchlorosilane formation. The reaction rate constant for methylchlorosilane formation is usually defined by those skilled in the art with the term "$K_p$". $K_p$ is the rate of methylchlorosilane production and is measured as grams of crude silane per grams of silicon per hour. A substantially high rate is linked to enhanced methylchlorosilane formation. A substantially high rate is typically greater than about 0.5 g silane/g Si—h.

The percent of methyldichlorosilane (MH) produced is also a measure of methylchlorosilane performance. The hydride in methyldichlorosilane likely derives from the cracking of the methyl chloride, which is indicative of a poorly performing methylchlorosilane reaction. Thus, substantially high methyldichlorosilane is linked to poor methylchlorosilane performance. In the present invention, substantially high methyldichlorosilane is typically greater than about above 2%.

Residue formed is also a measure of the performance of the methylchlorosilane reaction. A substantially low amount of residue is linked to enhanced methylchlorosilane formation. In the present invention, substantially low residue is typically lower than about 3%.

Commonly, the alkylhalosilane reaction may be practiced in a fixed bed reactor. However, the alkylhalosilane reaction can be conducted in other types of reactors, such as fluid bed and stirred bed. More specifically, the fixed bed reactor is a column that contains silicon particles through which alkyl halide gas passes. A stirred bed is similar to a fixed bed in which there is mechanical agitation of some sort in order to keep the bed in constant motion. A fluidized bed reactor typically includes a bed of the contact mass, silicon particles, catalyst particles and promoter particles, which is fluidized; i.e., the silicon particles are suspended in the gas, typically methylchloride, as it passes through the reactor. The alkylhalosilane reaction typically occurs under semi-continuous conditions or in batch mode at a temperature in a range between about 250° C. and about 350° C., and preferably between about 280° C. and about 320° C. It is also advisable to carry out the reaction under a pressure in a range between about 1 atmospheres and about 10 atmospheres in instances where a fluid bed reactor is used since higher pressure increases the rate of conversion of methyl chloride to methylchlorosilanes. Desirably, the pressure is in a range between about 1.1 atmospheres and about 3.5 atmospheres and preferably in a range between about 1.3 atmospheres and about 2.5 atmospheres.

The expression "semi-continuous conditions" with respect to the description of the reaction of silicon and alkyl halide in the presence of a catalyst means that the reaction is conducted in a fluid bed reactor under semi-continuous conditions. With a semi-continuous reaction, for example, the reactants are added and the reactor is run until about 50% of the silicon has been utilized. After about 50% silicon utilization, additional reactants of silicon and catalysts may be added. A semi-continuous reaction is in contrast to a batch mode reaction. With a batch mode reaction, all of the reactant components are combined and reacted until most of the reactants are consumed. In order to proceed, the reaction has to be stopped and additional reactants added. A fixed bed and stirred bed may both be run under batch conditions.

In order that those skilled in the art will be better able to practice the invention, the following examples are given by way of illustration and not by way of limitation.

EXAMPLES

The fixed bed reactor was used to carry out the alkylhalosilane reaction. The glass reactor was 100 mm long by 13 mm wide with a medium porosity glass frit located 80 mm from one end. Typically solid was loaded into the glass reactor and then heated under a flow of argon. The time zero of an experiment was when MeCl was turned on. The product was collected at a −20° C. condenser using a VWR model 1156 recirculating chiller. MeCl flow was controlled with a MKS model 1179 mass flow controller using Kel F seals and a MKS type 247 four channel read out. The furnace used was a A Nichrome$^R$-wire-wound glass tube heated in two zones with two separate Antech Sales model 59690 Watlow temperature controllers.

Silicon: Pulverized silicon with numerous trace elements was used. Particle size, size distribution, and trace element composition of the silicon are important in the Direct Process. To keep these variables under control, the same batch of silicon was used throughout this study. The silicon was produced by Elkem. A large quantity of this silicon was ground to surface area of 0.38 meters$^2$/gm. The elemental composition of the silicon is listed in the Table.

Major Components of Silicon Used in This Invention (ppm)

| Al | Ca | Fe | P |
|---|---|---|---|
| 1800 | 20 | 5000 | 40 |

Running the fixed bed reactor: A master batch of silicon powder and copper was prepared. Zinc was added to the master batch (30 mg), and 6 gms of master batch were loaded in the fixed bed reactor. The powder was lightly tapped so that the bed height was typically 4.7 to 4.9 cm. The reactor was installed in the system and argon flow was begun. The flow of argon was checked to be sure there were no system leaks. The bed was purged with argon for 2 hour at an argon flow rate of 40 cc/min (ca. 100 bed volumes). The heating system of the reactor was then turned on and typically within ½ hour the bed temperature had stabilized at 310° C., the nominal operating temperature. Argon was turned off, and MeCl flow at 35 cc/min was begun.

Silane vapor leaving the reactor was recovered in a condenser operating at −20° C. Liquid crude samples were periodically removed from the collector. The samples were weighed and later analyzed by gas chromatography using a HP 6890 gc equipped with an SPB210 capillary column (60 m×530 uM×3 uM film thickness).

The table below summarizes the powders evaluated. The benchmark catalyst was the copper flake used commercially. The OMG 831 had acceptable activity as a catalyst for the MCS reaction when compared to the Cu flake. Copper powder with high surface area and small particle size appears to be important for catalytic activity.

| Cu Source | How Made | BET ($m^2$/g) | D 50 (uM) | % Si utilization from lab MCS reactor |
|---|---|---|---|---|
| OMG 831 | Reduced CuxO from atomized process | 0.35 | 18.4 | 30 |
| USB D-101 | Spongy, Dendritic Electrolytic Cu | 0.36 | 43.3 | 4 |
| USB C-118 | Air Atomized | 0.03 | 35.9 | 2 |
| USB Cu155 | Water Atomized | 0.07 | 57.2 | trace |
| USB Cu278 | Water Atomized | 0.07 | 34.3 | 0 |
| Cu Flake | | 0.2 | | 50 |

OMG and USB (U.S. Bronze) are manufacturers of copper sources.

Figure 2:
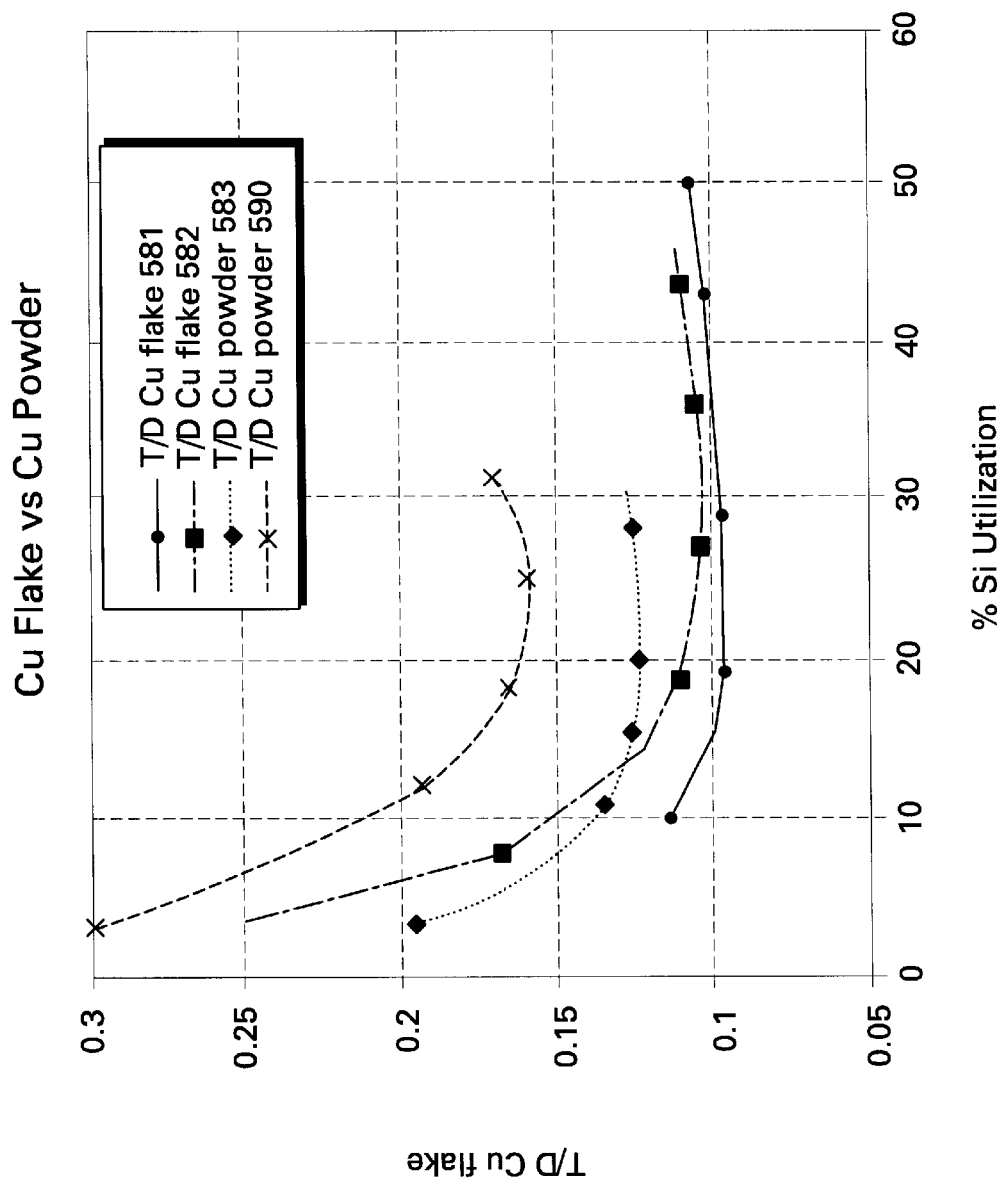
FIG. 2 shows the ratio of methylchlorosilane to dimethyldichlorosilane (T/D) produced from duplicate runs of the methylchlorosilane reaction using either copper flake catalyst or copper powder catalyst.
Figure 3:
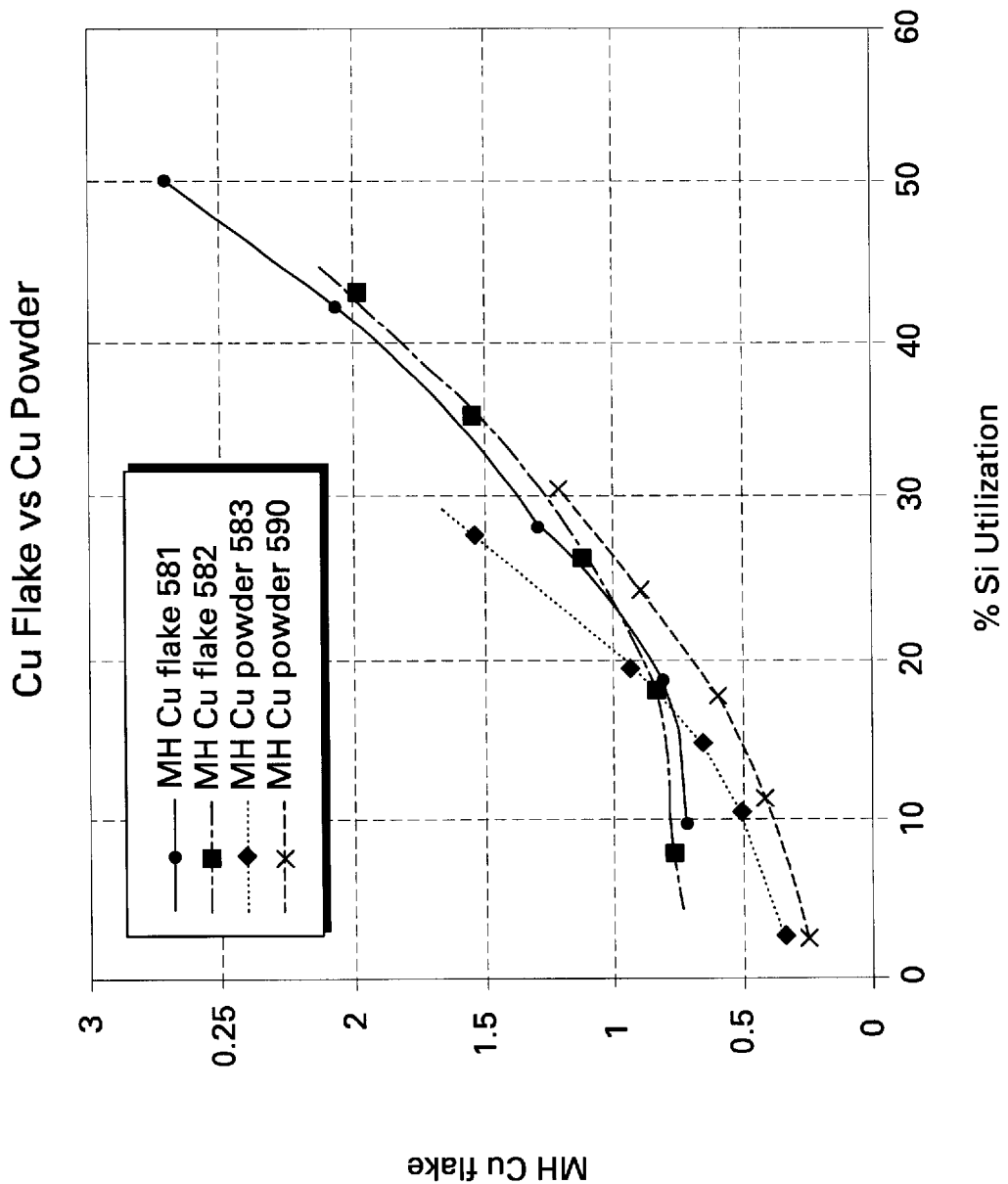
FIG. 3 shows weight percent of methyldichlorosilane produced from duplicate runs of the methylchlorosilane reaction using either copper flake catalyst or copper powder catalyst.
Figure 4:
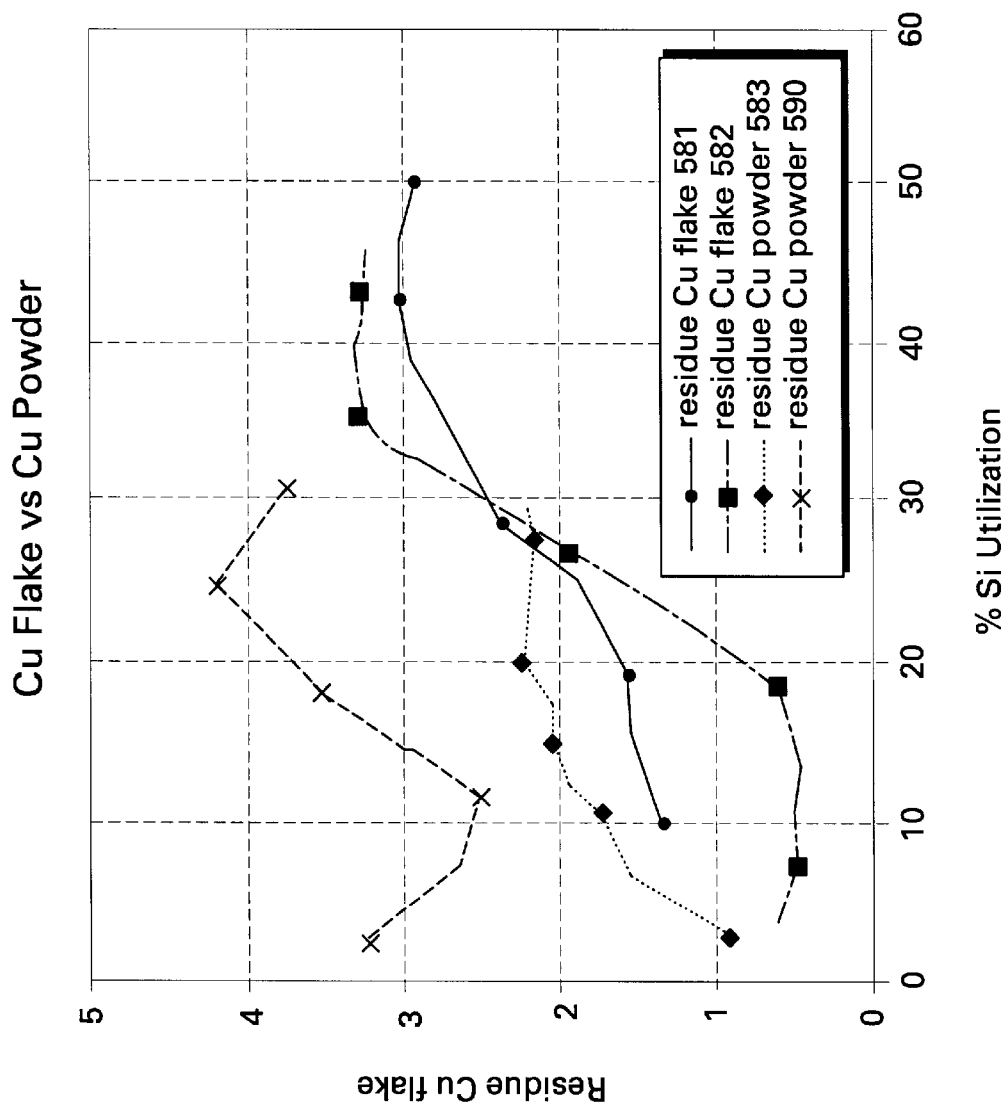
FIG. 4 shows weight percent of residue produced from duplicate runs of the methylchlorosilane reaction using either copper flake catalyst or copper powder catalyst.

FIGS. 1–4 show the results of duplicate runs using either copper flake catalyst or copper OMG 831 powder catalyst in the MCS reaction. The copper flake catalyst and the copper powder catalyst of the present invention are capable of yielding methylchlorosilane product, maintaining selectivity toward dimethyldichlorosilane, and maintaining a substantially low amount of methylchlorosilane residue that is formed.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A method for making alkylhalosilanes comprising reacting an alkyl halide and silicon in the presence of a copper catalyst comprising spongy, dendritic electrolytic copper and at least one co-catalyst.

2. The method in accordance with claim 1, wherein the alkyl halide is methyl chloride.

3. The method in accordance with claim 1, wherein said reaction is conducted in a fluid bed reactor.

4. The method in accordance with claim 1, wherein said reaction is conducted in a fluid bed reactor.

5. The method in accordance with claim 1, wherein said reaction is conducted in a stirred bed reactor.

6. The method in accordance with claim 1, wherein the reaction is operated in a batch mode.

7. The method in accordance with claim 1, wherein the reaction is conducted at a temperature in a range between about 250° C. and about 350° C.

8. The method in accordance with claim 1, wherein the reaction is conducted at a temperature in a range between about 280° C. and about 320° C.

9. The method in accordance with claim 1, wherein the copper catalyst is present in a range between about 10% and about 60% by weight relative to the entire reactor bed.

10. The method in accordance with claim 1, wherein the copper catalyst is present in a range between about 15% and about 45% by weight relative to the entire reactor bed.

11. The method in accordance with claim 1, wherein the copper catalyst is present in a range between about 20% and about 40% by weight relative to the entire reactor bed.

12. The method in accordance with claim 1, wherein the copper catalyst has a surface area greater than about 0.2 square meters per gram ($m^2$/g).

13. The method in accordance with claim 1, wherein the silicon is powdered.

14. A method for making methylchlorosilanes comprising reacting methyl chloride and powdered silicon in the presence of a copper catalyst comprising spongy, dendritic electrolytic copper and at least one co-catalyst comprising zinc, tin, antimony, phosphorus, or combinations thereof.

* * * * *